Jan. 21, 1969 J. M. GARABEDIAN Plant Pat. 2,858
PLUM TREE
Filed July 19, 1967
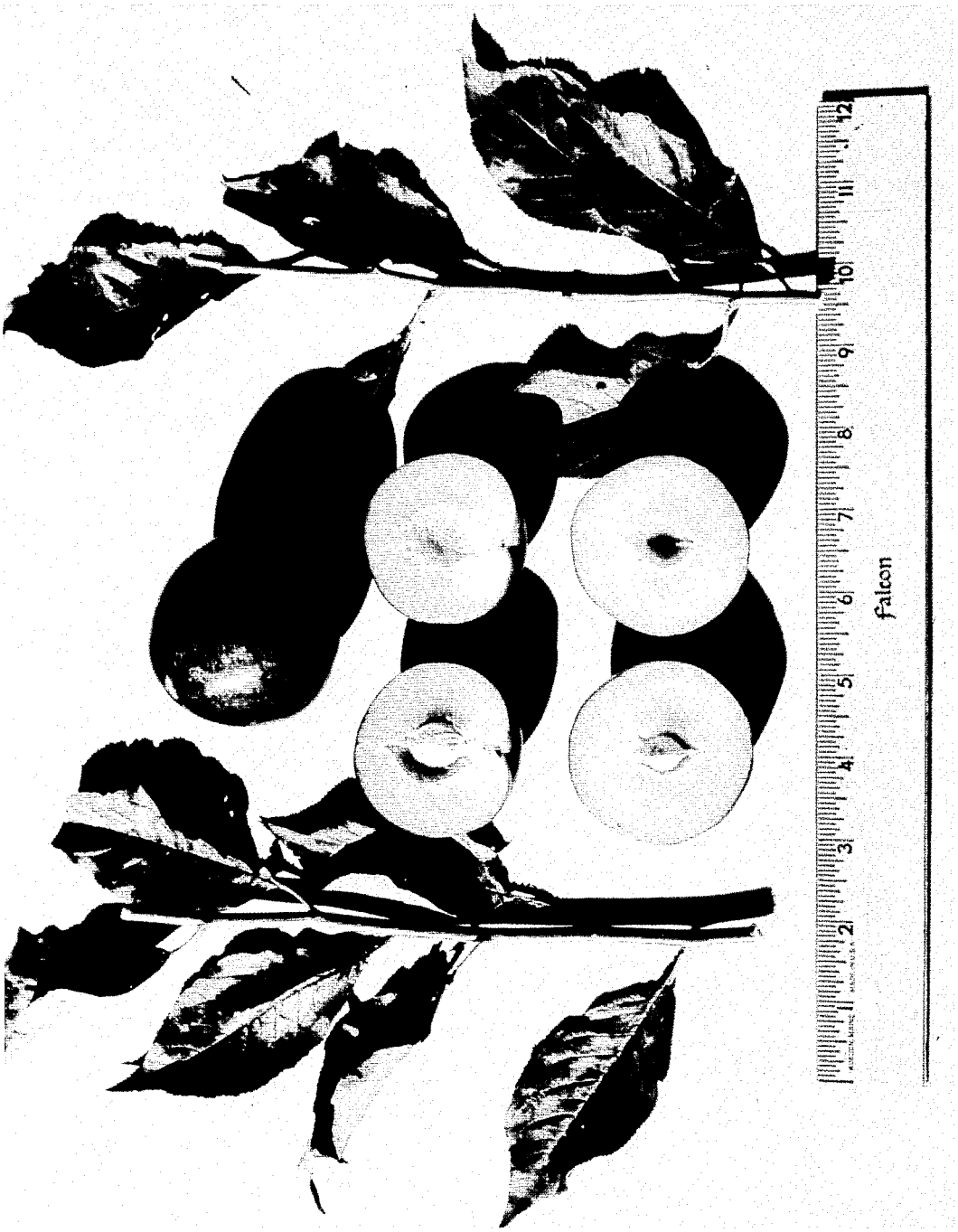
INVENTOR
John M. Garabedian
BY
Webster & Webster
ATTORNEYS United States Patent Office Plant Pat. 2,858
Patented Jan. 21, 1969

2,858
PLUM TREE

John M. Garabedian, Fresno, Calif., assignor to Peach & Willow Farms, Fresno, Calif., a corporation of California Filed July 19, 1967, Ser. No. 654,665
U.S. Cl. Plt.—38 1 Claim
Int. Cl. A01h 5/08

ABSTRACT OF THE DISCLOSURE

A new and distinct variety of plum tree which bears large, freestone fruit having straw-yellow flesh shading to red, and skin having a yellow ground color substantially entirely overspread with deep red shading to black.

*Origin of the variety.*—Seeds resulting from an open pollinated cross were gathered from trees of the El Dorado (unpatented) plum in an orchard located on my ranch in Madera County, Calif. The hybrid seeds as thus gathered were planted in a nursery plot located on my ranch in Fresno County, Calif.; the resultant seedlings—which were open pollinated—having been maintained under close observation by me. One of such open pollinated seedlings evidenced distinctive characteristics which made it desirable for commercial growing, and such seedling—which is the present variety—was, therefore, selected by me for asexual reproduction.

*Asexual reproduction of the variety.*—I accomplished asexual reproduction of the present variety of plum tree by multiple budding on a mature nectarine tree in an orchard located on the aforesaid ranch in Fresno County, Calif.; such reproduction having run true to the original tree in all respects.

*Summary of the variety.*—The present variety of plum tree is characterized by the regular bearing of large, freestone, very symmetrical, generally globose fruit which has more similarity in form to the Laroda (unpatented) than to the El Dorado. Further, the fruit—which is of good quality for dessert use (delicaate, subacid, and mild in flavor)—ripens about thirty-five days after the El Dorado under like growing conditions; the skin of the fruit having a straw-yellow ground color substantially entirely overspread with a deep red shading to black, while the flesh (which is yellow) has substantially more red than the El Dorado, and which red shades from relatively deep (at the apex) to a lighter red (extending nearly to the shoulder of the fruit).

*Brief description of the drawing.*—The drawing is an illustration, by photographic reproduction in color, of fruit of the variety together with leaves thereof; the view including one fruit cut in half in the suture plane and another fruit cut in half at a right angle to the suture plane, the stone remaining in one half of each cut fruit.

*Description of the variety.*—The botanical details of this new and distinct variety of plum tree—with color definitions (except those in common color terms) referenced to Maerz and Paul Dictionary of Color—are as follows:

Tree:
- *Size.*—Large.
- *Vigor.*—Vigorous.
- *Growth.*—Upright to spreading.
- *Density.*—Dense to open.
- *Form.*—Vase-shaped.
- *Hardiness.*—Hardy.
- *Production.*—Medium.
- *Bearing.*—Regular bearer.

Trunk:
- *Size.*—Stocky.
- *Texture.*—Medium.

Branches:
- *Size.*—Medium.
- *Texture.*—Medium.
- *Color.*—Dorsal side—Brown (15–C–12). Ventral side—Glossy Green (21–L–6).
- *Lenticels.*—Number—medium.
- *Size.*—Small.

Leaves:
- *Size.*—Large. Length—4⅜" to 5¼", average 4⅞". Width—1⅝" to 1 15/16", average 1¾".
- *Form.*—Usually elliptical, some oval, and some lanceolate.
- *Leaf base.*—Narrow acute to acute.
- *Leaf apex.*—Mostly acuminate, sharply acute to taper pointed.
- *Thickness.*—Medium.
- *Texture.*—Smooth.
- *Leaf veins.*—Pinnately net veined.
- *Margin.*—Glandular, reddish globose glands at apex of serrations. Finely crenate.
- *Petiole.*—Length—long. Size—medium. Color: dorsal side—Green (21–K–6); ventral side—Green (21–J–5).
- *Glands.*—Average number—1 to 3, usually 2. Some opposite—mostly irregular. Medium size; usually globose, some mixed; green; positioned on petiole at base of blade.
- *Stipules.*—0 to 1, usually none. Length—⅛" to 3/16".
- *Leaf buds.*—Small; round.
- *Leaf color.*—Dorsal side—Medium Green (24–L–9). Ventral side—Lighter Green (23–E–6).

Flower buds:
- *Hardiness.*—Hardy.
- *Size.*—Small.
- *Length.*—Short.
- *Form.*—Plump; free.
- *Surface.*—Very light pubescence.

Flowers:
- *Blooming period.*—Date of first bloom—Mar. 4, 1967. Date of full bloom—Mar. 11, 1967; medium, as compared with other varieties; approximately 6 days after Santa Rosa (unpatented).
- *Size.*—Small. Spread across petals—20–26 mm., average 25 mm.
- *Calyx lobes.*—Small. Sepals—green. Reddish-colored glands on each of calyx lobes.
- *Stamens.*—24 to 34, average 27.
- *Color.*—White.

Fruit:
- *Maturity when described.*—Eating hard (Aug. 4, 1966).
- *Date of first picking.*—Aug. 8, 1966.
- *Date of last picking.*—Aug. 16, 1966.
- *Size.*—Very uniform; large. Diameter axially—2" to 2¼", average 2⅛". Transversely in suture plane—2" to 2¼", average 2⅛".
- *Form.*—Very uniform; symmetrical; globose. Transversely through diameter—usually round but sometimes to slightly elliptical.
- *Suture.*—A distinct line; very shallow; extends from base to beyond but discontinues at apex; noticeable apex tip beyond pistil point; dark suture stripe, more noticeable on some fruit.
- *Ventral surface.*—Rounded strongly.
- *Lips.*—Usually equal, a few unequal.
- *Cavity.*—Rounded; abrupt; circular, with suture showing on both sides. Average depth—¼". Average breadth—¾". Markings—light strain to pink color, covered with bloom.

*Base.*—Truncate.
*Apex.*—Truncate.
*Pistil point.*—Oblique.
*Stem.*—Small. Average length—5/16". Average width—1/16". Easily detached from fruit; very short brush.

Skin:
*Thickness.*—Thin.
*Texture.*—Medium; very slightly bitter.
*Tenacity.*—Tenacious to flesh.
*Tendency to crack.*—None in dry season.
*Color.*—Straw Yellow (11–G–2) substantially entirely overspread with a Deep Red (6–L–3) shading to black. Heavy Bluish-Gray bloom (46–A–6).

Flesh:
*Amygdalin.*—Wanting.
*Juice.*—Moderate; rich.
*Texture.*—Firm; fine; crisp.
*Fibers.*—Few; fine; tender.
*Ripens.*—Evenly.
*Flavor.*—Subacid; mild; delicate.
*Aroma.*—Very slight.
*Eating quality.*—Very good.
*Color.*—Straw Yellow (11–E–2) with red shading from relatively deep (4–L–10) at apex to a lighter red toward the shoulder of the fruit; there being more red next to the skin throughout, and in the flesh on the sunny side of the fruit. Surface of pit cavity—yellow to pink.

Stone:
*Type.*—Free—adheres to flesh very slightly along both dorsal and ventral edges. Free on sides toward base. Short fibers. Retains short fiber-like theads along wing near base on ventral edge.
*Size.*—Medium. Average length—7/8". Average breadth—5/8". Average thickness—3/8".
*Form.*—Globose; full cuneate toward base.
*Base.*—Straight—unsymmetrical bulge and wing oblique to ventral edge.
*Hilum.*—Narrow; oval.
Apex.—Rounded—slightly elongated, with mucronate tip about 1/16" in length.

*Sides.*—Slightly unequal; curved on left side (to ventral edge).
*Surface.*—Regularly furrowed near base; ridged near base; pitted throughout.
*Pits.*—Usually circular, some angular.
*Ventral edge.*—Thick, with wing toward ventral side and base.
*Dorsal edge.*—Narrow, with deep narrow groove toward base to above center.
*Ridges.*—On either side—interrupted. Mostly short at base and jagged toward base.
*Kernel.*—Ovate; slightly bitter; usually viable, some not. Average width—3/8". Average length—1/2".
*Seed coat.*—Pellicle—Yellow (10–G–3). Amygdalin—moderate.
*Thickness of pit wall.*—Average—3/32".
*Tendency to split.*—None in dry season.
*Color.*—Beige (11–C–3).

Use: Dessert.
Keeping quality: Good.
Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is a regular bearer of large, freestone, very symmetrical, generally globose fruit bearing more similarity in form to the Laroda than the El Dorado; characterized by yellow flesh shading from a relatively deep red at the apex to a lighter red extending nearly to the shoulder of the fruit, and straw-yellow skin substantially entirely overspread with red shading to black; and further characterized by a harvest period which is about thirty-five days after the El Dorado under like growing conditions.

No references cited.

ROBERT E. BAGWILL, *Primary Examiner.*